(12) United States Patent
Blanchard

(10) Patent No.: US 7,931,609 B2
(45) Date of Patent: Apr. 26, 2011

(54) EXTREMITY SUPPORT APPARATUS AND METHOD

(76) Inventor: Christophe Blanchard, Brooklyn, NY (US)

(*) Notice: Subject to any disclaimer, the term of this patent is extended or adjusted under 35 U.S.C. 154(b) by 163 days.

(21) Appl. No.: 12/196,130

(22) Filed: Aug. 21, 2008

(65) Prior Publication Data

US 2010/0049110 A1 Feb. 25, 2010

(51) Int. Cl.
*A61F 5/00* (2006.01)
(52) U.S. Cl. .................. 602/21; 602/20; 602/5
(58) Field of Classification Search ............... 602/5, 16, 602/20, 21
See application file for complete search history.

(56) References Cited

U.S. PATENT DOCUMENTS

| | | | |
|---|---|---|---|
| 3,810 A | 10/1844 | Roe | |
| 3,859 A | 12/1844 | Post | |
| 50,128 A | 9/1865 | Hudson | |
| 183,376 A | 10/1876 | Darrach | |
| 1,334,596 A | 3/1920 | Crouch | |
| 1,340,630 A | 5/1920 | Maddox | |
| 3,683,897 A | 8/1972 | Shield et al. | |
| 3,976,057 A | 8/1976 | Barclay | |
| 4,050,456 A | 9/1977 | Cornue | |
| 4,055,171 A | 10/1977 | Ries | |
| 4,612,919 A | 9/1986 | Best | |
| 4,763,901 A | 8/1988 | Richter | |
| 4,875,677 A | 10/1989 | Tetreault | |
| 5,116,296 A | 5/1992 | Watkins et al. | |
| 5,167,612 A | 12/1992 | Bonutti | |
| 5,330,417 A | 7/1994 | Petersen et al. | |
| 5,337,737 A | 8/1994 | Rubin et al. | |
| 5,352,190 A | 10/1994 | Fischer et al. | |
| 5,365,947 A | 11/1994 | Bonutti | |
| 5,456,268 A | 10/1995 | Bonutti | |
| 5,554,104 A | 9/1996 | Grim | |
| 5,683,336 A | 11/1997 | Pape | |
| 5,685,830 A | 11/1997 | Bonutti | |
| 5,782,780 A | 7/1998 | Mason et al. | |
| 5,865,714 A | 2/1999 | Marlowe | |
| 6,117,097 A | 9/2000 | Ruiz | |
| 6,203,511 B1 | 3/2001 | Johnson et al. | |
| 6,533,741 B1 | 3/2003 | Lee et al. | |
| 6,537,237 B1 | 3/2003 | Hopkins et al. | |
| 6,666,837 B2 | 12/2003 | Weihermuller | |
| 6,783,555 B2 | 8/2004 | Kuhn et al. | |
| 6,821,259 B2 | 11/2004 | Rahman et al. | |
| 6,866,646 B2 | 3/2005 | Hopkins et al. | |
| 6,936,020 B2 | 8/2005 | Davis | |
| 7,048,704 B2 | 5/2006 | Sieller et al. | |
| 7,261,679 B2 | 8/2007 | Sload | |
| 2003/0125651 A1 | 7/2003 | Hopkins et al. | |
| 2004/0010213 A1 | 1/2004 | Gregory et al. | |
| 2004/0049139 A1 | 3/2004 | Craciunescu | |
| 2006/0241539 A1 | 10/2006 | Agrawal et al. | |
| 2007/0010772 A1 | 1/2007 | Ryan | |
| 2007/0106189 A1 | 5/2007 | Salmon et al. | |

FOREIGN PATENT DOCUMENTS

DE 43 00 522 A1 4/1994

*Primary Examiner* — Patricia M Bianco
*Assistant Examiner* — Camtu T Nguyen
(74) *Attorney, Agent, or Firm* — Law Office of Peter G. Korytnyk, PLLC

(57) ABSTRACT

An extremity support apparatus having a second cuff, a first cuff, a bridge rod attached to the second cuff, and a tension rod attached to the first cuff and to the bridge rod is provided. The extremity support apparatus can place the support a first cuff in a cantilevered manner when a distal portion and a proximal portion of an extremity are supported in respective first and second cuffs. A method of supporting an extremity in a non-weight-bearing manner is also provided.

20 Claims, 6 Drawing Sheets

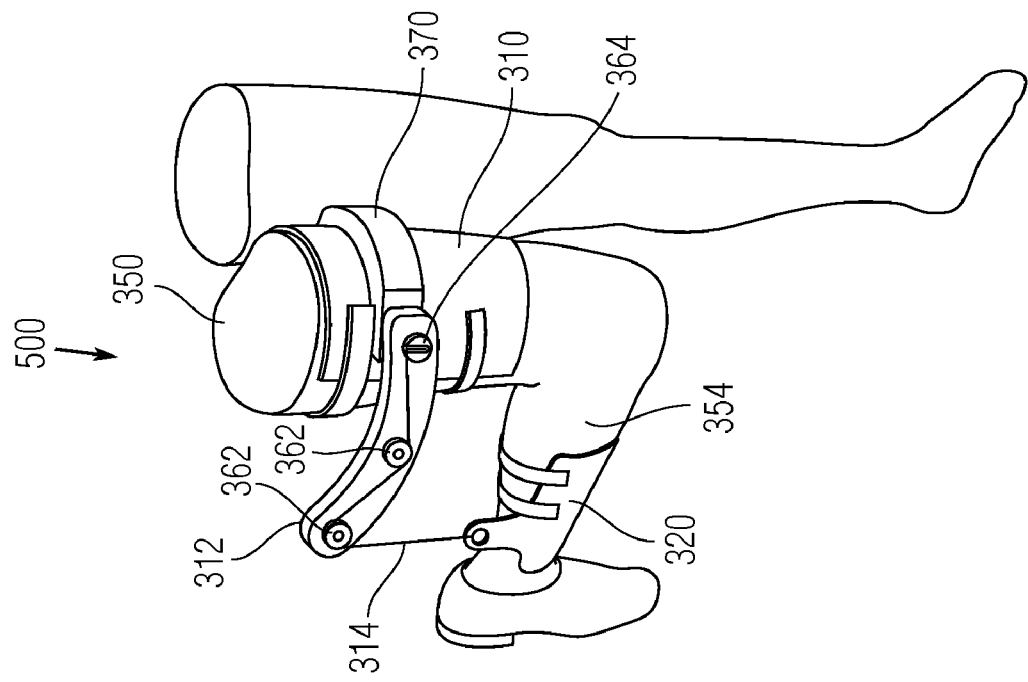
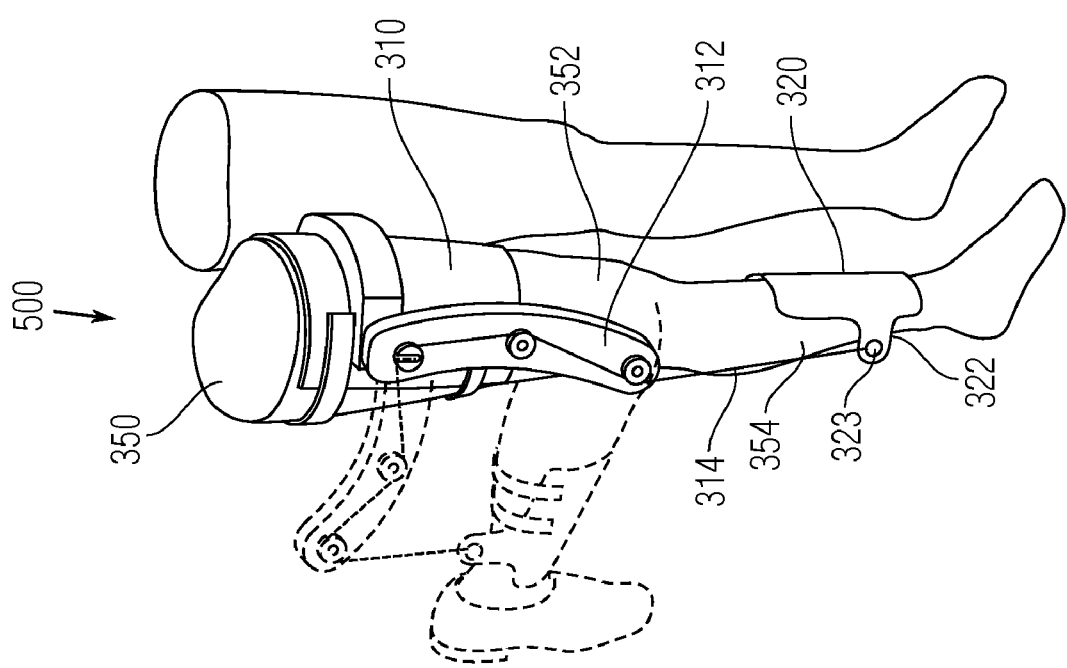
Fig. 5B
Fig. 5A

EXTREMITY SUPPORT APPARATUS AND METHOD

FIELD OF THE INVENTION

The present teachings relate to an extremity support apparatus and a method of using same. In particular, the present teachings relate to an extremity support apparatus that provides support to an extremity that requires isolation, elevation, immobilization, or that cannot support a load so that the extremity can heal properly. The extremity support apparatus of the present teachings can support the extremity by forming a cantilevered support for the distal portion of the extremity.

BACKGROUND OF THE INVENTION

Arm and leg slings are useful to isolate a limb while the limb heals. Prior art mechanical arm slings can require a cloth or fabric loop that hangs over the shoulder of a patient to support the limb while the limb is immobilized by the mechanical sling. The cloth or fabric loop is undesirable because the cloth or fabric loop causes stress on the neck or shoulder that can cause additional injuries leading to cervical spine damage and neuropathy. Prior art leg slings that include an over-the-shoulder cloth or fabric loop also suffer from similar problems.

Prior art bulky-sponge armrest devices that include bulky self-adhering hook-and-loop fasteners are undesirable because the prior art devices are not durable, not storable, and are not reusable. Furthermore, the devices are susceptible to harboring bacteria and viral particles that can cause disease or illness. These prior arts devices are not hypoallergenic and can therefore cause rashes, itching, or other skin discomfort.

Prior art hands-free crutch alternatives to traditional crutches or traditional walkers can cause knee inflammation or swelling that can lead to stress fractures of the patella.

Accordingly, there is a need for an extremity support apparatus that does not cause injury or discomfort through use, while isolating, elevating, and/or immobilizing the extremity.

SUMMARY OF THE INVENTION

According to an embodiment, an extremity support apparatus can include a first cuff, a second cuff, a bridge rod extendable outwardly from the second cuff, and a tension rod extendable between the first cuff and the bridge rod. The bridge rod and the tension rod can be capable of forming a cantilever support for the first cuff when a distal portion and a proximal portion of an extremity are supported in the respective first and second cuffs.

According to another embodiment, an extremity support apparatus can include a first cuff capable of supporting a distal portion of an extremity, a second cuff capable of supporting a proximal portion of the extremity, and a cantilever support structure operatively arranged between the first cuff and the second cuff. The cantilever support structure can be configurable to support the first cuff and corresponding distal extremity portion in a cantilevered manner and arrange the first cuff in a fixed relation with respect to the second cuff when the distal and proximal portions of the extremity are supported in the respective first and second cuffs.

A further embodiment includes a method of immobilizing a joint of an extremity using an extremity support apparatus. The method can include providing a first cuff, providing a second cuff including a bridge rod extendable outwardly therefrom, providing a tension rod extendable between the first cuff and the bridge rod, removably affixing a first cuff to a distal portion of the extremity, and removably affixing a second cuff to a proximal end of the extremity. The method can include adjusting one or more of the bridge rod and the tension rod to support the first cuff and corresponding distal extremity portion in a cantilevered manner and arrange the first cuff in a fixed relation with respect to the second cuff.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE DRAWINGS

FIG. 5a depicts a perspective view of an extremity support apparatus of the present teachings adapted to support a leg;

FIG. 5b depicts a perspective view of an extremity support apparatus of the present teachings adapted to support a leg.

Figure 1:
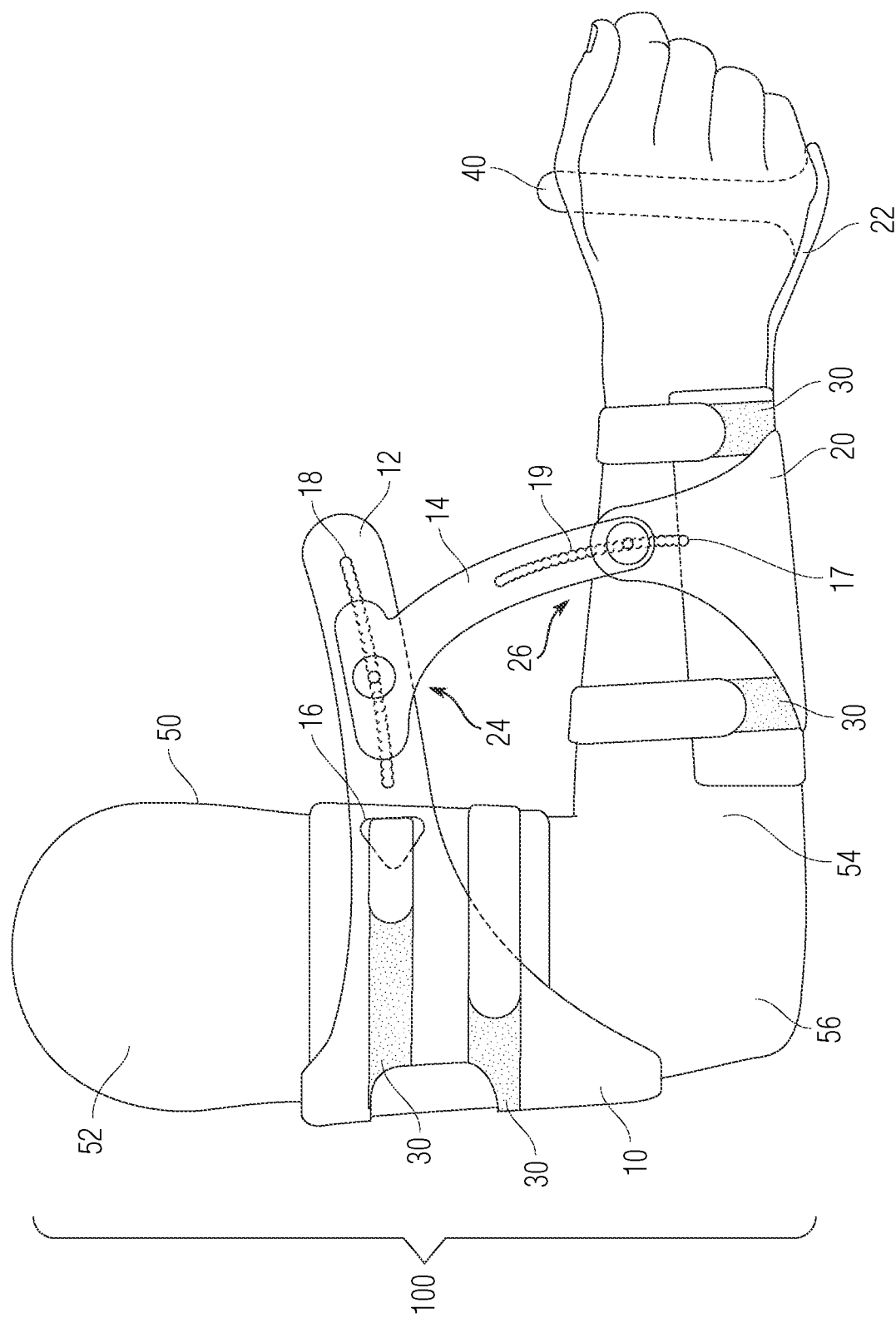
FIG. 1 depicts a side view of an extremity support apparatus of the present teachings adapted to support an arm.

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

Terms of anatomical direction and the human body, as used herein, have their generally accepted meaning within the anatomical and medical arts as used in standard reference texts, such as, for example, Gray's Anatomy, $39^{th}$ Ed., by Susan Standring, available from Elsevier/Churchill Livingstone.

As shown in FIGS. 1-6 and according to various embodiments, an extremity support apparatus 100 can include a first cuff 20, a second cuff 10, a bridge rod 12 extendable outwardly from the second cuff 10, and a tension rod 14 extendable between the first cuff 10 and the bridge rod 12. The bridge rod 12 and the tension rod 14 can be capable of forming a cantilever support for the first cuff 20 when a distal portion 54 and a proximal portion 52 of an extremity 50 are supported in the respective first and second cuffs.

The tension rod 14 can be in tension and supported by the bridge rod 12 when the distal portion 54 of an extremity 50 is arranged in the first cuff 20 and the proximal portion 52 of the extremity 50 is arranged in the second cuff 10. The bridge rod 12 and the tension rod 14 can be securable to place the first cuff 20 in a fixed relation with respect to the second cuff 10. The first cuff 20 can include a palm rest 22, a palm handle 40, or both.

Figure 2:
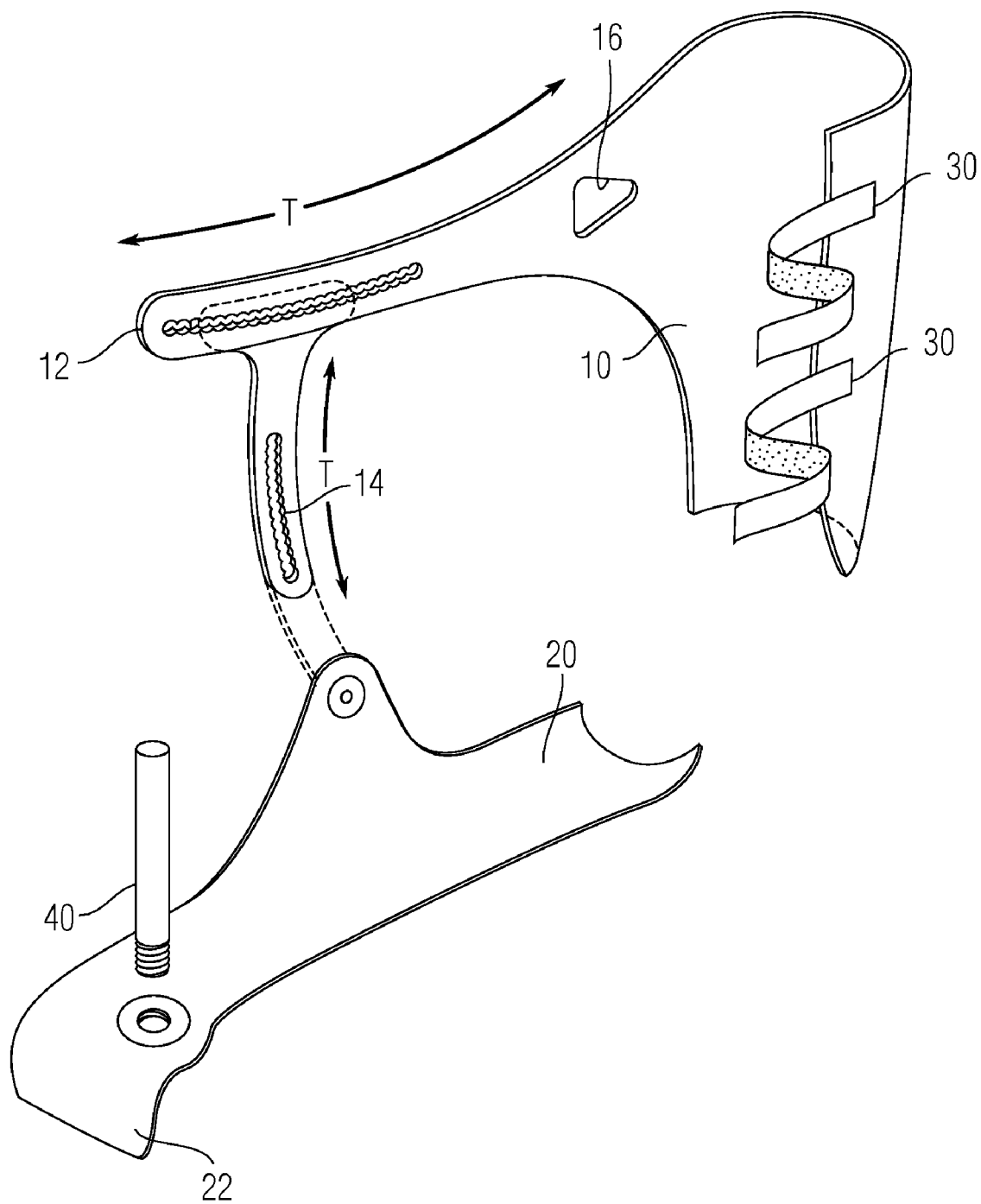
FIG. 2 depicts a perspective exploded view of the extremity support apparatus of FIG. 1.

The bridge rod 12 and the tension rod 14 can be adjustably securable. The bridge rod 12 and the second cuff 10 can form an integral one-piece structure, as shown in FIGS. 1 and 2. An interface 24 between the bridge rod 12 and the tension rod 14 can be adjustable. An interface 26 between the tension rod 14 and the first cuff 20 can be adjustable.

As shown in FIGS. 5A and 5B, the tension rod 314 can be a cable. Furthermore, the bridge rod 312 can be pivotable such that the cantilever support for the first cuff 320 is adjustable.

More particularly, in reference to FIG. 1, an extremity elevating device 100 is shown according to various embodiments. The extremity elevating device 100 can include a second cuff 10. Second cuff 10 can contact the triceps area of the proximal portion 52 of an upper extremity 50. Second cuff 10 can wrappingly contact the proximal portion 52 of an upper extremity 50. More specifically, second cuff 10 can contact the proximal portion 52 in the region of the upper extremity 50 that includes the triceps brachii muscle (not shown). Second cuff 10 can be used to secure the proximal portion 52 in a fixed position such that the medial joint of the upper extremity (e.g. the elbow) does not flex or otherwise move when the extremity support apparatus is secured to the extremity 50.

According to various embodiments, the second cuff 10 can include at least one fastening strap 30 that can secure the second cuff 10 to the proximal end 52 of the extremity 50. The fastening strap 30 can run around the proximal end 52 in a transverse manner. The fastening strap 30 can be in an open, unstrapped position or in a closed, strapped position. When the fastening strap 30 is functioning to secure the second cuff 10 to the proximal end 52, the fastening strap 30 is in a closed, strapped position. The fastening strap 30 can be constructed of or can include, for example, a length of a hook-and-loop fastener. The fastening strap 30 can be permanently affixed to the second cuff 10 such that the fastening strap 30 remains attached to the second cuff 10 when the fastening strap 30 is in an open, unstrapped position.

According to various embodiments, second cuff 10 can include pass-through 16. Pass-through 16 is adapted such that fastening strap 30 can run from a first side of second cuff 10 to a second side of second cuff 10 through pass-through 16 while, for example, fastening strap 30 is in a closed, strapped position while functioning to secure second cuff 10 to proximal end 52.

Second cuff 10 can include a bridge rod 12 that extends parallel to the coronal plane at the proximal portion 52 when the upper extremity 50 is in standard anatomical position. According to various embodiments, the bridge rod 12 can be less flexible than other portions of the second cuff 10. The bridge rod 12 can be less flexible because, for example, the chemical composition of a polymer comprising the bridge rod 12 differs from the chemical composition of a polymer comprising other portions of the second cuff 10. The bridge rod 12 can be less flexible because, for example, the monomeric units comprising the bridge rod 12 differs from the monomeric units comprising the other portions of the second cuff 10. The bridge rod 12 can be less flexible because, for further example, the cross-section of the bridge rod 12 is thicker than the cross-section of the other portions of the second cuff 10.

The bridge rod 12 can include an adjustable track portion 18. The adjustable track portion 18 is adapted to adjustably receive an end of a tension rod 14. One or more first or second surfaces of the adjustable track portion 18 can be scored, textured, roughened, grooved, sunken, or otherwise adapted to receive the end of the tension rod 14 such that, at the interface 24 of the adjustable track portion 18 and the end of the tension rod, one of the adjustable track portion 18 and the tension rod 14 or both are discouraged from moving in a slidable manner when the extremity support apparatus 100 is in use.

The adjustable track portion 18 is adapted to receive a bolt or other hardware piece (not shown) that can be loosened and tightened to adjust the angle of the medial joint (e.g., elbow or knee) of an extremity held in an extremity support apparatus of the present teachings. The adjustable track portion 18 can have raised detents or bumps within the track portion adapted to prevent the bolt or other hardware piece from sliding within the adjustable track portion 18.

The extremity elevating device 100 can include a first cuff 20. First cuff 20 can contact the distal portion 54 of the upper extremity 50. First cuff 20 can wrappingly contact the distal portion 54 of the upper extremity 50. More specifically, first cuff 20 can contact the distal portion 54 in the region of the upper extremity 50 that includes the two long bones of the forearm, the radius and the ulna (not shown). A first cuff 20 can be used to secure the forearm in a fixed position such that the medial joint (e.g. the elbow or knee) does not flex or otherwise move when the extremity support apparatus 100 is secured to the extremity 50.

According to various embodiments, the first cuff 20 can include at least one fastening strap 30 that can secure the first cuff 20 to the distal end 54 of the extremity 50. The fastening strap 30 can run around the distal end 54 in a transverse manner. The fastening strap 30 can be in an open, unstrapped position or in a closed, strapped position. When the fastening strap 30 is functioning to secure the first cuff 20 to the distal end 54, the fastening strap 30 is in a closed, strapped position. The fastening strap 30 can be constructed of or can include, for example, a length of a hook-and-loop fastener. The fastening strap 30 can be permanently affixed to the first cuff 20 such that the fastening strap 30 remains attached to the first cuff 20 when the fastening strap 30 is in an open, unstrapped position.

The first cuff 20 can include an adjustable track portion 17. The adjustable track portion 17 can be adapted to adjustably receive an end of a tension rod 14. One or more first or second surfaces of the adjustable track portion 17 can be scored, textured, roughened, grooved, sunken, or otherwise adapted to receive the end of the tension rod 14 such that the interface 26 of the adjustable track portion 17 and the end of the tension rod 14 does not move in a slidable manner when the extremity support apparatus 100 is in use.

The adjustable track portion 17 is adapted to receive a bolt or other hardware piece (not shown) that can be loosened and tightened to adjust the angle of the medial joint (e.g., elbow or knee) of an extremity held in an extremity support apparatus of the present teachings. The adjustable track portion 17 can have raised detents or bumps within the track portion adapted to prevent the bolt or other hardware piece from sliding within the adjustable track portion 17.

Alternatively, or in addition to the adjustable track portion 17, the first cuff 20 can include a non-sliding attachment point (not shown). The non-sliding attachment point can join the first cuff 20 to the tension rod 14. The non-sliding attachment point can be opened or loosened to adjust the extremity support apparatus 100 to properly fit the device 100 to the extremity 50. The non-sliding attachment point can be closed or tightened to secure the extremity 50 in the desired location. The non-sliding attachment point can be, for example, a bolt, a screw, or other attachment hardware.

As shown in FIGS. 1 and 2, the first cuff 20 can include a palm rest 22. The palm rest 22 can be adapted to prevent or reduce movement of the distal or inferior radioulnar joint. The palm rest 22 can be ergonomically shaped such that the palm of the hand of the extremity 50 naturally falls into the palm rest 22 and the fingers of the hand of the extremity 50 curl naturally around the palm rest 22. The palm rest 22 can be engineered in any way to support the hand or otherwise reduce the mobility of the hand, or both, in a comfortable manner. For example, the palm rest 22 can include sides (not shown) or other means to support the hand from movement when a body is in a recumbent position. For further example, the palm rest 22 can include sides (not shown) or other means to support the hand from movement when a body is in an upright position.

According to various embodiments, the palm rest 22 can include palm handle 40. The palm handle 40 can be permanently or removabley affixed to the palm rest 22. The palm handle 40 can be adapted, for example, to hold the hand of an extremity such that the hand rests in a position perpendicular to the hand position when used only with palm rest 22.

As previously disclosed above, the extremity support apparatus 100 can include a tension rod 14. The tension rod 14 can be adapted to adjust the angle of a medial joint (e.g., an elbow or a knee) and to hold said joint in non-moving manner. One or both ends of the tension rod 14 can seat, mate, or otherwise connect to the second cuff 10, the bridge rod 12, the first cuff 20, the palm rest 22, the palm handle 40, or combinations thereof. The tension rod 14 can connect to at least one of the second cuff 10, the bridge rod 12, the first cuff 20, the palm rest 22, the palm handle 40 in a moveable, adjustable, fixed, or non-moveable manner. The tension rod 14 can be adapted to allow for different lengths of an extremity 50. For example, tension rod 14 can adjustably connect to the bridge rod 12, the first cuff 20, or both. For further example, tension rod 14 can un-movably connect to the bridge rod 12, the first cuff 20, or both.

The tension rod 14 can include an adjustable track portion 19. One or both first or second surfaces of the adjustable track portion 19 can be scored, textured, roughened, grooved, sunken, or otherwise adapted to receive the end of the tension rod 14 such that at the interface 26 of the adjustable track portion 19 and the end of the tension rod 14, the adjustable track portion 19 and the tension rod 14 are discouraged from moving in a slidable manner when the extremity support apparatus 100 is in use.

The adjustable track portion 19 is adapted to receive a bolt or other hardware piece (not shown) that can be loosened and tightened to adjust the angle of the medial joint (e.g., elbow or knee) of an extremity held in an extremity support apparatus of the present teachings. The adjustable track portion 19 can have raised detents or bumps within the track portion adapted to prevent the bolt or other hardware piece from sliding within the adjustable track portion 19.

Figure 3:
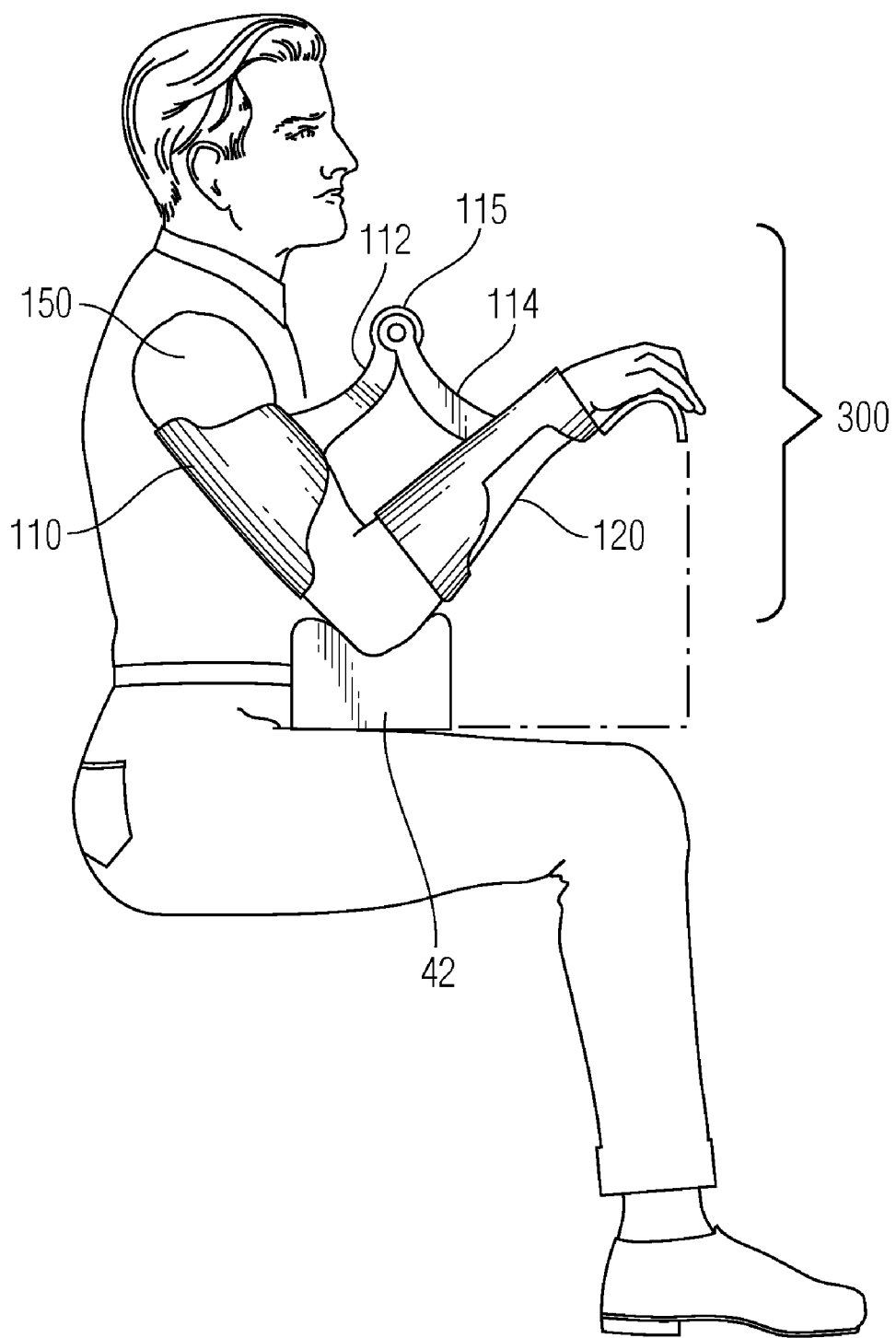
FIG. 3 depicts a side view of an extremity support apparatus of the present teachings adapted to support an arm in an elevated position.

As shown in FIG. 3, an extremity support apparatus 300 of the present teachings is shown being used to elevate an extremity 150 while a user is in a seated position. An elbow pad 42 can be utilized in conjunction with the present teachings to comfortably support an extremity 150 when held in place with extremity support apparatus 300. According to various embodiments, the second cuff 110 and the first cuff 120 are connected by a bridge rod 112 and a tension rod 114. Bridge rod 112 and tension rod 114 connect at adjustable joint 115. Adjustable joint 115 can be loosened or tightened to adjust extremity support apparatus 300 to the desired fitment and positioning of extremity 150. According to various embodiments, the bridge rod 112 and tension rod 114 can be adjusted at the interface of bridge rod 112 and second cuff 110, tension rod 114 and first cuff 120, or both.

Figure 4:
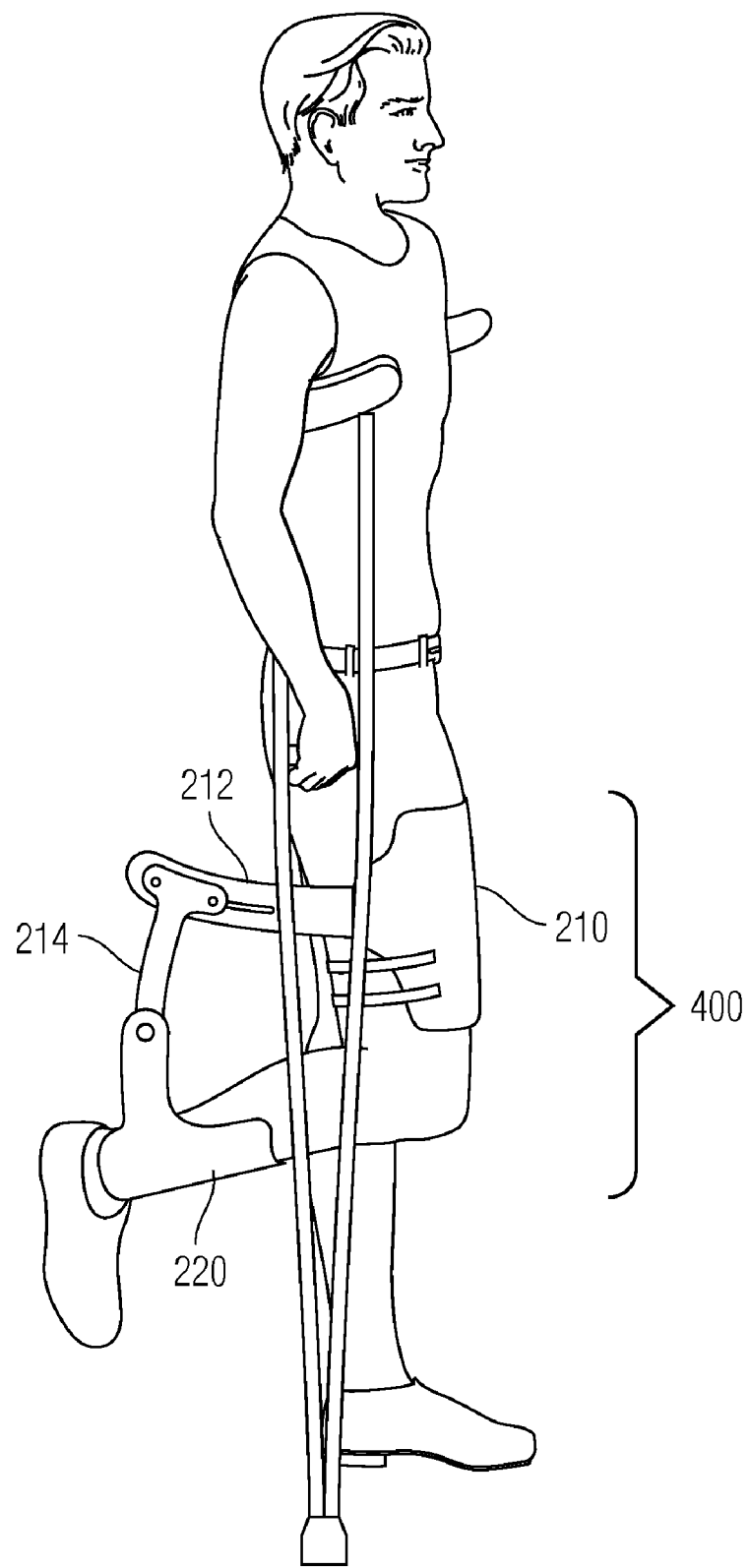
FIG. 4 depicts a side view of an extremity support apparatus of the present teachings adapted to support a leg.

As shown in FIG. 4, an extremity support apparatus 400 of the present teachings can support a lower extremity, according to various embodiments. The extremity support apparatus 400 can include a second cuff 210, a bridge rod 212, a first cuff 220, and a tension rod 214. The structure and function of second cuff 210, bridge rod 212, first cuff 220, and tension rod 214, as shown in FIG. 4, can be similar to second cuffs, bridge rods, first cuffs, and tension rods, respectively, as disclosed elsewhere herein, according to various embodiments.

As shown in FIG. 5a and FIG. 5b, an extremity support apparatus 500 can support a lower extremity 350. The extremity support apparatus 500 can include a first cuff 320, a second cuff 310, and a bridge rod 312. The structure and function of first cuff 320, second cuff 310, bridge rod 312, and tension rod 314 can be similar to first cuffs, second cuffs, bridge rods, and tension rods, respectively, as disclosed elsewhere herein, according to various embodiments.

The first cuff 320 can include a flange portion 322. Flange portion 322 can include an attachment point 323. Attachment point 323 can be a hole, grommet, rivet, hook, eyelet, or the like. Attachment point 323 can be adapted to rotatively or pivotably connect to a tension rod 314 such that tension rod 314 can be arranged substantially parallel to the proximal region 352 of the lower extremity 350. Tension rod 314 can be fixedly or removably attached to attachment point 323. Tension rod 314 can be, for example, a cable, a cord, or the like.

Bridge rod 312 can be adjustably attached to a support base 370. Bridge rod 312 can be in a deployed position such that the length of the bridge rod 312 is substantially perpendicular to the length of the proximal region 352 of the lower extremity 350, the bridge rod 312 can be pivoted into a retracted position such that the length of the bridge rod 312 is substantially parallel to the length of the proximal region 352, or the bridge rod 312 can be arranged somewhere in between a deployed position and a retracted position.

Bridge rod 312 can be used to support the tension rod or cable 314. Tension rod 314 can be attached to first cuff 320 and run to an end of bridge rod 312 and then to a second end of bridge rod 312. Tension rod 314 can run through one or more run points 362. One or more run points 362 can distribute the load of tension rod 314 and support tension rod 314 when bridge rod 312 is in a deployed position or in a position other than a retracted position. One or more run points 362 can be used to guide the tension rod 314 through bridge rod 312 or can be used to keep the tension rod 314 from slipping, tangling, or otherwise fouling the run of tension rod or cable 314.

Tension rod 314 can be attached on at least one end by a tensioner (not shown). The tensioner can be incorporated in or separate from bridge rod 312. The tensioner can be used to keep tension on tension rod 314. The tensioner can be operated manually, for example, by a crank 364. The crank 364 can be folded when not in use, such that the crank handle does not snag or catch on an article of clothing or the like. The tensioner can be operated manually, for example, by inserting a hex wrench (not shown) into a hex bolt (not shown). The tensioner can be an automatic tensioner such that a constant force, for example, in pounds, is put on tension rod 314. The constant force, for example, can be varied based on the desired force, or the like. The constant force can vary based on whether the bridge rod 312 is in a deployed position or in a retracted position, for example.

According to various embodiments, the extremity support apparatus 500 can keep a lower extremity 350 in a non-weight bearing position, for example, such that the knee is bent and the distal portion 354 is held off the ground when the patient is generally upright. According to various embodiments, the angle of a leg formed by the distal portion 354 relative to the proximal portion 352 can be adjusted by cranking the crank handle 364 (shown in a folded position) to shorten or lengthen the tension rod 314 while the bridge rod 312 is in a deployed position or a position other than a retracted position.

The support base 370 can be affixed to the second cuff 310 such that second cuff 310 can be wrappingly fitted to the proximal region 352 of the lower extremity 350. The second cuff 310 can be designed to fit a range of proximal region diameters that can vary from patient to patient. Support base 370 can be adapted to enable rotation or pivoting of bridge rod 312. According to various embodiments, bridge rod 312 can be rotated or pivoted to at least a first and a second position. According to various embodiments, bridge rod 312 can be rotated or pivoted through a range of positions or can be rotated through multiple discrete positions. Support base 370 can have a locked position, an unlocked position, or both, such that the bridge rod 312 can be prevented from rotating or pivoting, freely allowed to rotate or pivot, or both. Support base 370 can have a range of tensions such that the force used to discourage or impair the movement of bridge rod 312, or otherwise increase the force of friction on the interface of the bridge rod 312 and the support base 370, can be varied. The tension or force to control the movement of bridge rod 312 can be varied with, for example, a wrench, knob, a lever arm, or the like. The support base 370 can have one or more detents such that the tension bridge support can have one or more discrete positions with respect to the support base 370.

Figure 6:
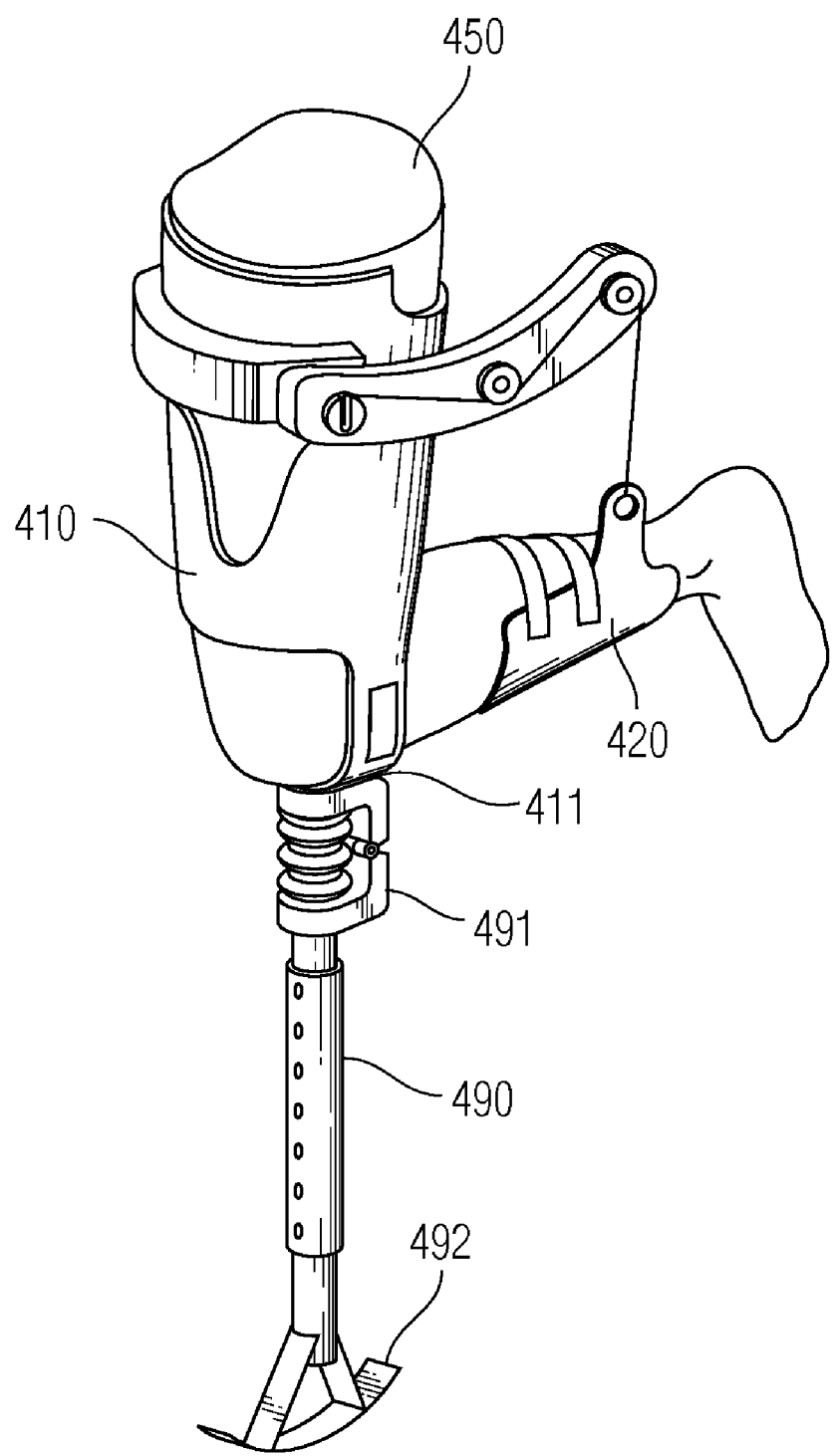
FIG. 6 depicts a perspective view of an extremity support apparatus of the present teachings including a leg crutch.

As shown in FIG. 6, the second cuff 410 can have an accessory attachment portion 411. Alternatively, the first cuff 420 can be provided with an accessory attachment portion. Accessory attachment portion 411 can include a receiving end to securely receive accessories. Accessory attachment portion 411 can be adapted to removabley affix accessories such as, for example, leg crutch 490.

The length of leg crutch 490 can be varied such that a patient can walk comfortably without the use of extremity 450 as a weight-bearing support. Leg crutch 490 can be a fixed length. Leg crutch 490 can be adjusted through the use of, for example, conventional means of adjusting crutches that are known in the art. The leg crutch can be adjusted using, for example, an adjustable collar (not shown) or the like. Leg crutch 490 can include a shock absorber 491, according to various embodiments. Shock absorber 491 can be in parallel with the length of leg crutch 490 and can cushion the stress of a footing 492 striking the ground. Footing 492 can be arched, curved, contoured, or the like such that the patient can obtain and maintain a consistent walking or running stride while attached to the extremity support apparatus 400 of the present teachings. A bottom side portion of footing 492 that contacts the ground can have a surface that discourages slipping or skidding of the footing 492. For example, the bottom portion can be made of rubber designed for gripping. For further example, the bottom portion can be contoured or can have divots, dimples, or the like to promote firm contact and discourage skidding or slipping.

According to various embodiments, an extremity support apparatus can include a first cuff capable of supporting a distal portion of an extremity, a second cuff capable of supporting a proximal portion of the extremity, and a cantilever support structure operatively arranged between the first cuff and the second cuff. The cantilever support structure can be configurable to support the first cuff and corresponding distal extremity portion in a cantilevered manner and arrange the first cuff in a fixed relation with respect to the second cuff when the distal and proximal portions of the extremity are supported in the respective first and second cuffs.

The cantilever support structure can include a bridge rod arranged with the second cuff and a tension rod arranged with the first cuff. The tension rod can be in tension and supported by the bridge rod when the distal portion of an extremity is arranged in the first cuff and the proximal portion of the extremity is arranged in the second cuff. The bridge rod and the tension rod can be securable to place the first cuff in a fixed relation with respect to the second cuff. The bridge rod and the second cuff can form an integral one-piece structure.

One or more components of an elevated extremity device, such as, for example, a second cuff, a first cuff, a bridge rod, a tension rod, and combinations thereof, can be made of a hypoallergenic material. The aforementioned components can be made of an ultraviolet (UV) resistant material.

The aforementioned components can be made of a rigid or semi-rigid material. For example, the aforementioned components can be made of polypropylene, fiberglass, polyurethane, any other suitable plastic material, or combinations thereof.

The aforementioned components can be rigid or semi-rigid. The aforementioned components can be constructed using any suitable thickness or formulation to support an extremity in a fixed manner such that the extremity cannot be moved about the medial joint (i.e., knee or elbow) and that the extremity cannot be used as a weight-bearing limb, e.g., in a non-weight-bearing manner.

According to various embodiments, portions of the extremity support apparatus that contact the skin or clothing of the extremity can contain at least one pad or padding in a location between the skin or clothing of the extremity and the portions of the extremity support apparatus. The padding can be, for example, one of a foam-type padding, a pillow-type padding, a thick fabric-type padding, combinations thereof, or the like. The padding can be removabley affixed to or permanently affixed to the portions of the various embodiments of the extremity support apparatus of the present teachings. The removabley affixed padding can be removabley affixed using, for example, double-sided tape, a length of hook and loop fastener, combinations thereof, or the like.

According to various embodiments, portions of the extremity support apparatus of the present teachings that contact the skin or clothing of an extremity can be covered with a natural or synthetic fabric. The fabric covering can be tightly fitted around the portions such that the fabric covering does not bunch, gather, slide, or otherwise move when the portions are in close contact with the skin or clothing of the extremity.

The fabric covering can be made from a fabric that is infused with or otherwise contains at least one of an antibacterial agent, an antimicrobial agent, and an antifungal agent to ensure that the fabric does not harbor pathogens. The fabric cover can include any combination of natural fibers, synthetic fibers, synthetic fibers containing an antibacterial agent, synthetic fibers containing an antimicrobial agent, and synthetic fibers containing an antifungal agent. Methods of making an antibacterial fiber are disclosed, for example, in U.S. Pat. No. 5,458,906 and in Int'l. Pat. Pub. No. WO 1996/000321, which are incorporated herein by reference in their entireties. Methods of making an antimicrobial or antifungal fiber are disclosed, for example, in U.S. Pat. Nos. 6,841,244 and 6,723,428, which are incorporated herein by reference in their entireties.

According to various embodiments, the fabric covering can be made from a fabric that is infused with or otherwise contains a scent such that the fabric covering emits a pleasant smell. For example, the fabric covering can be woven with fibers containing SENSORY PERCEPTION TECHNOLOGY, available from Woolmark Development International Ltd, United Kingdom.

A method of immobilizing a joint of an extremity can be provided. The method can include providing a first cuff, providing a second cuff including a bridge rod extendable outwardly therefrom, providing a tension rod extendable between the first cuff and the bridge rod, removably affixing a first cuff to a distal portion of the extremity, and removably affixing a second cuff to a proximal end of the extremity. The method can include adjusting one or more of the bridge rod and the tension rod to support the first cuff and corresponding distal extremity portion in a cantilevered manner and arrange the first cuff in a fixed relation with respect to the second cuff.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein

What is claimed is:

1. An extremity support apparatus, comprising:
a first cuff shaped to support a distal end of an extremity along a first axis;
a second cuff shaped to support a proximal end of an extremity along a second axis;
a bridge rod extendable outwardly from the second cuff in a cantilevered fashion and being fixed with respect to the second cuff such that the bridge rod defining a static non-zero angle with the second axis in a cantilevered fashion; and
a tension rod extendable generally vertically between the first cuff and the cantilevered bridge rod;
wherein the bridge rod and the tension rod are capable of forming a cantilever support for the first cuff whereby the tension rod is extendable generally downwardly from the cantilevered bridge rod to the first cuff when a distal portion and a proximal portion of an extremity are supported in the respective first and second cuffs.

2. The extremity support apparatus of claim 1, wherein the tension rod is in tension and supported by the bridge rod when the distal portion of the extremity is arranged in the first cuff and the proximal portion of the extremity is arranged in the second cuff.

3. The extremity support apparatus of claim 2, wherein the bridge rod and the tension rod are securable to place the first cuff in a fixed relation with respect to the second cuff.

4. The extremity support apparatus of claim 3, wherein the bridge rod and the tension rod are adjustably securable.

5. The extremity support apparatus of claim 1, wherein the bridge rod and the second cuff form an integral one-piece structure.

6. The extremity support device of claim 1, wherein a first interface between the bridge rod and the tension rod is adjustable.

7. The extremity support device of claim 6, wherein a second interface between the tension rod and the first cuff is adjustable.

8. The extremity support device of claim 1, wherein the tension rod is a cable.

9. The extremity support device of claim 8, wherein the bridge rod is pivotable such that the cantilever support for the first cuff is adjustable.

10. The extremity support device of claim 1, wherein the first cuff includes a palm handle.

11. The extremity support device of claim 1, further comprising a leg crutch operatively arranged with at least one of the first cuff and the second cuff.

12. An extremity support apparatus, comprising:
a first cuff capable of supporting a distal portion of an extremity along a first axis;
a second cuff capable of supporting a proximal portion of the extremity; and
a cantilever support structure operatively arranged between the first cuff and the second cuff, the cantilever support structure including a bridge rod extendable in a cantilevered fashion from the second cuff and being fixed with respect to the second cuff such that the bridge rod defining a static non-zero angle with the second axis and a tension rod extendable generally downwardly from the cantilevered bridge rod to the first cuff;
wherein the cantilever support structure is configurable to support the first cuff and corresponding distal extremity portion in a cantilevered manner and arrange the first cuff in a fixed relation with respect to the second cuff when the distal and proximal portions of the extremity are supported in the respective first and second cuffs.

13. The extremity support apparatus of claim 12, wherein the tension rod is in tension and supported by the bridge rod when the distal portion of an extremity is arranged in the first cuff and the proximal portion of the extremity is arranged in the second cuff.

14. The extremity support apparatus of claim 13, wherein the bridge rod and the tension rod are securable to place the first cuff in a fixed relation with respect to the second cuff.

15. The extremity support apparatus of claim 13, wherein the tension rod is a cable.

16. The extremity support apparatus of claim 15, wherein the bridge rod is pivotable such that the cantilever support for the first cuff is adjustable.

17. The extremity support apparatus of claim 12, wherein the bridge rod and the second cuff form an integral one-piece structure.

18. The extremity support apparatus of claim 12, wherein a first interface between the bridge rod and the tension rod is adjustable.

19. The extremity support apparatus of claim 18, wherein a second interface between the tension rod and the first cuff is adjustable.

20. A method of immobilizing a joint of an extremity, comprising:
providing a first cuff shaped to support a distal end of an extremity along a first axis;
providing a second cuff shaped to support a proximal end of an extremity along a second axis and including a bridge rod extendable outwardly therefrom in a cantilevered fashion and being fixed with respect to the second cuff such that the bridge rod defining a static non-zero angle with the second axis;
providing a tension rod extendable generally vertically between the first cuff and the bridge rod;
removably affixing the first cuff to the distal portion of the extremity;
removably affixing the second cuff to the proximal end of the extremity; and
adjusting one or more of the bridge rod and the tension rod to support the first cuff and corresponding distal extremity portion in a cantilevered manner whereby the tension rod extends generally downwardly from the cantilevered bridge rod to the first cuff and the first cuff is in a fixed relation with respect to the second cuff.

* * * * *